US005723668A

United States Patent [19]
Buschmann et al.

[11] Patent Number: 5,723,668
[45] Date of Patent: Mar. 3, 1998

[54] METHOD OF SEPARATING THE RACEMATE OF TRAMADOL

[75] Inventors: Helmut Buschmann; Werner Winter, both of Aachen; Ivars Graudums, Stolberg; Peter Jansen, deceased, late of Eschweiler, all of Germany, by Ursula Jansen, heiress

[73] Assignee: Gruenenthal GmbH, Aachen, Germany

[21] Appl. No.: 775,396

[22] Filed: Dec. 31, 1996

[30] Foreign Application Priority Data

Jan. 19, 1996 [DE] Germany ............... 196 01 745.9

[51] Int. Cl.$^6$ ................................................ C07B 57/00
[52] U.S. Cl. .................................... 564/304; 564/307
[58] Field of Search ........................... 564/304, 307

[56] References Cited

U.S. PATENT DOCUMENTS

| | | | |
|---|---|---|---|
| 2,528,267 | 10/1950 | Dearborn et al. | 564/304 |
| 3,652,589 | 3/1972 | Flick et al. | 564/304 |
| 4,138,403 | 2/1979 | Howarth et al. | 260/307 FA |

OTHER PUBLICATIONS

Jacques et al., *Enantiomers, Racemates and Resolutions,* Krieger Publishing, Malebar, Florida (1991), pp. 259–261 and 387–388.

*Primary Examiner*—Peter O'Sullivan
*Attorney, Agent, or Firm*—Evenson, McKeown, Edwards & Lenahan P.L.L.C.

[57] ABSTRACT

A method of separating the racemate of tramadol is disclosed.

9 Claims, No Drawings

METHOD OF SEPARATING THE RACEMATE OF TRAMADOL

This invention relates to a method of separating the racemate of tramadol. Tramadol hydrochloride—(1RS, 2RS)-2-dimethylaminomethyl-1-(3-methoxy-phenyl)-cyclohexanol hydrochloride—assumes a special position amongst centrally acting analgesics, since this active ingredient acts as a strong inhibitor of pain without the side effects which are known for opioids (J. Pharmacol. Exp. Ther. 267, 331 (1993)). Tramadol is a racemate and consists of equal amounts of (+)- and (−)-enantiomers. It is known that the enantiomers of tramadol have an interesting pharmaceutical profile which differs from that of tramadol. The (+)-enantiomer is characterised by an opiate-like analgesic effect which is considerably enhanced compared with that of tramadol, whilst a significant inhibition of noradrenaline reassimilation is observed with the (−)-enantiomer.

The preparation of tramadol enantiomers using the racemate separation reagent dibenzoyl-tartaric acid is described in Arzneim.-Forsch./Drug Res. 28 (I), 114 (1978). A disadvantage of this method is the use of the very expensive chiral auxiliary reagent dibenzoyl-tartaric acid. This compound can only be re-used in the racemate separation with considerable difficulties, since during the alkaline work-up of the diastereoisomeric salts the dibenzoyl groups are partially split off. Moreover, the optical antipodes of dibenzoyl-tartaric acid are required for the isolation of the tramadol enantiomers: in order to obtain the (+)-enantiomer of tramadol, precipitation has to be effected with (−)-O,O'-dibenzoyl-L-tartaric acid; in order to obtain the (−)-enantiomer of tramadol, precipitation has to be effected with (+)-O,O'-dibenzoyl-D-tartaric acid.

The underlying object of the present invention was therefore to develop a method of separating the racemate of tramadol with which the tramadol enantiomers can be obtained in constant high yields and with high enantiomer purities, whilst avoiding the known disadvantages which are associated with the use of dibenzoyl-tartaric acid.

It has surprisingly been found that the severe demands imposed on the method to be developed are fulfilled with the use of inexpensive L-(+)-tartaric acid.

Accordingly, the present invention relates to a method of separating the racemate of tramadol, which is characterised in that a racemic tramadol salt is converted into the base, the (−)-enantiomer of tramadol is separated by precipitation with L-(+)-tartaric acid, and the (+)-enantiomer of tramadol is isolated from the mother liquor from tartaric acid precipitation by releasing the tramadol base and subsequent conversion into a salt which is different from tartrate.

Racemic tramadol hydrochloride is particularly suitable as a starting material for the method according to the invention. This is converted into racemic tramadol in an aqueous solution by the addition of alkali hydroxides, preferably sodium hydroxide, and extraction with an organic solvent, for example dichloromethane and/or diethyl ether. The base obtained is subsequently treated with L-(+)-tartaric acid, preferably in the presence of an organic solvent, most preferably in the presence of an aliphatic $C_{1-5}$ alcohol. The tartrate of the (−)-enantiomer of tramadol which forms is separated, particularly by crystallisation, from the tartrate of the (+)-tramadol enantiomer formed, and is subsequently isolated if desired by releasing the tramadol base under the aforementioned conditions and conversion into a tramadol salt which is different from the tartrate, preferably into the hydrochloride.

The (+)-tramadol enantiomer which is soluble in the mother liquor in the form of the tartrate salt is isolated by releasing the tramadol base under the aforementioned conditions and subsequent conversion into a salt which is not a tartrate, particularly into tramadol hydrochloride.

Conversion of the tramadol base into the hydrochloride can be effected with concentrated hydrochloric acid or gaseous hydrogen chloride in an organic solvent, for example acetone, dioxane, diethyl ether and/or diisopropyl ether, or with trimethylchlorosilane/water in a solvent, for example 2-butanone.

The method according to the invention can be carried out economically and in an environmentally friendly manner. Compared with racemate separation with dibenzoyl-tartaric acid, the method according to the invention is distinguished in that only one enantiomeric form of tartaric acid, namely the inexpensive L-(+)-tartaric acid, is necessary for separating the racemate. With L-(+)-tartaric acid the enantiomers can be obtained in a yield of more than 85% with respect to the racemate used, and with an enantiomer purity greater than 98%. Moreover, L-(+)-tartaric acid has a formula weight which is less by a factor of 2.4 than that of dibenzoyl-tartaric acid, with the result that the precipitation products which are formed are considerably reduced. In addition, the mother liquor can be recycled to the racemate separation process after releasing the tramadol base.

EXAMPLES

Example 1

(−)-(1S,2S)-2-dimethylaminomethyl-1-(3-methoxy-phenyl)-cyclohexanol hydrochloride (−1)

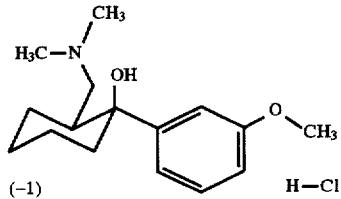

1st step: release of the racemic base 3 kg (10 mole) (1RS,2RS)-2-dimethylaminomethyl-1-(3-methoxy-phenyl)-cyclohexanol hydrochloride (1) were suspended in 4800 ml water and treated with 1.6 kg crushed ice. 1300 ml of 36–38% (technical) caustic soda solution were added drop-wise with stirring. The mixture was subsequently extracted with 7000 ml dichloromethane, and was extracted with a further 2000 ml dichloromethane after phase separation. The combined organic phases were dried over sodium sulphate. After removing the solvent by distillation, 2630 g (99% theoretical) of (1RS,2RS)-2-dimethylaminomethyl-1-(3-methoxy-phenyl)-cyclohexanol were obtained as a syrup.

2nd stage: precipitation with L-(+)-tartaric acid 2630 g (10 mole) of the base from the first step were dissolved in 2400 ml ethanol and treated with a solution consisting of 1500 g (10 mole) L-(+)-tartaric acid and 11.200 ml ethanol. The mixture was stirred for two hours at room temperature and allowed to stand for 24 hours at 4° C. to effect crystallisation. The precipitated crystals were filtered off under suction and washed with 6400 ml ethanol at 4° C. After drying the crystalline material at room temperature in vacuum (60 mbar), 2050 g (49% with respect to the total amount of racemic base used) of (1S,2S)-2-dimethylaminomethyl-1-(3-methoxy-phenyl)-cyclohexanol L-(+)-tartrate with a melting point of 173°–175° C. were obtained (specific rotation: $[\alpha]^{RT}_D = -12.2°$ (c=1.01; methanol)).

3rd step: release of the base from the L-(+)-tartaric acid salt 2050 g (4.95 mole) (1S,2S)-2-dimethylaminomethyl-1-(3-methoxy-phenyl)-cyclohexanol L-(+)-tartrate from step 2 were dissolved in 4000 ml water and treated with 900 g crushed ice. 1000 ml of 36–38% (technical) caustic soda solution were added drop-wise with stirring. The mixture was subsequently extracted with 2500 ml dichloromethane, and was extracted with a further 500 ml dichloromethane after phase separation. The combined organic phases were dried over sodium sulphate. After removing the solvent by distillation, 1280 g (99% theoretical) of (1S,2S)-2-dimethylaminomethyl-1-(3-methoxy-phenyl)-cyclohexanol were obtained as a syrup.

4th step: conversion of (1S,2S)-2-dimethylaminomethyl-1-(3-methoxy-phenyl)-cyclohexanol into the hydrochloride (−1)

1280 g (4.86 mole) of the base obtained from step 3 were dissolved in 16 l 2-butanone and were treated with 88 ml (4.9 mole) water and 621 ml (532 g; 4.9 mole) trimethyl-chlorosilane with stirring. The mixture was stirred for 3 hours at room temperature and allowed to stand for 24 hours at 4° C. to effect crystallisation. The precipitated solid was filtered off under suction, washed with 5000 ml 2-butanone at 4° C. and dried to constant weight at 90° C. under vacuum (60 mbar). 1390 g (95% theoretical with respect to the base from step 3 which was used, and 92% with respect to the enantiomer content of the racemate from step 1 which was used) of hydrochloride (−1) were obtained as colourless crystals.

| Melting point: | 172–173° C. |
|---|---|
| Specific rotation: | $[\alpha]^{RT}_D = -29.6°$ (c = 1.00; methanol). |

Example 2

(+)-(1R,2R)-2-dimethylaminomethyl-1-(3-methoxy-phenyl)-cyclohexanol hydrochloride (+1)

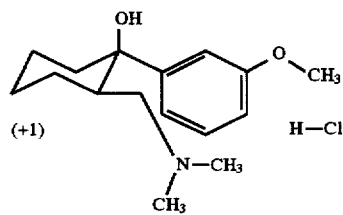

1st step: release of the base from the mother liquor from L-(+)-tartaric acid precipitation The ethanolic mother liquor and the washing phase from L-(+)-tartaric acid precipitation (Example 1, 2nd step) were combined. After removing the solvent by distillation, the residue (2080 g) was dissolved in 2500 ml water and treated with 900 g crushed ice. 1000 ml of 36–38% (technical) caustic soda solution were added drop-wise with stirring. The mixture was subsequently extracted with 2700 ml dichloromethane, and was extracted with a further 600 ml dichloromethane after phase separation. The combined organic phases were dried over sodium sulphate. After removing the solvent by distillation, 1340 g (99% theoretical) of (1R,2R)-2-dimethylaminomethyl-1-(3-methoxy-phenyl)-cyclohexanol were obtained as a syrup.

2nd step: conversion of (1R,2R)-2-dimethylaminomethyl-1-(3-methoxy-phenyl)-cyclohexanol into the hydrochloride (+1)

1340 g (5.09 mole) of the base obtained from step 1 were dissolved in 17.5 l 2-butanone and treated with 105 ml (5.8 mole) water and with 670 ml (573 g; 5.3 mole) trimethyl-chlorosilane with stirring. The mixture was stirred for 3 hours at room temperature and allowed to stand for 24 hours at this temperature to effect crystallisation. The precipitated solid was filtered off under suction, washed with 5000 ml 2-butanone and dried to constant weight at 90° C. under vacuum (60 mbar). 1350 g (88% theoretical with respect to the base from step 1 which was used, and 89% with respect to the enantiomer content of the racemate from Example 1, step 1 which was used) of hydrochloride (+1) were obtained as colourless crystals.

| Melting point: | 171–172° C. |
|---|---|
| Specific rotation: | $[\alpha]^{RT}_D = -29.6°$ (c = 1.00; methanol). |

We claim:

1. A method of separating a racemate of tramadol into (−)-tramadol enantiomer and (+)-tramadol enantiomer fractions, said method comprising the steps of:

converting a racemic tramadol salt into a racemic tramadol free base solution;

separating (−)-tramadol enantiomer from the racemic free base solution by selective precipitation thereof with L-(+)-tartaric acid to leave a mother liquor containing (+)-tramadol enantiomer;

releasing (+)-tramadol enantiomer free base from the mother liquor; and converting the (+)-tramadol enantiomer free base into a non-tartrate salt.

2. A method according to claim 1, wherein said racemic tramadol salt is racemic tramadol hydrochloride.

3. A method according to claim 1, wherein said precipitation with L-(+)-tartaric acid is effected in the presence of an organic solvent.

4. A method according to claim 3, wherein said organic solvent is an aliphatic $C_{1-5}$ alcohol.

5. A method according to claim 1, wherein the (−)-tramadol enantiomer is separated by crystallization.

6. A method according to claim 1, wherein said non-tartrate salt is a hydrochloride salt.

7. A method of resolving a racemic tramadol salt into (−) and (+) enantiomer fractions, said method comprising the steps of:

a) adding alkali hydroxide to a solution of the racemic tramadol salt to convert the salt into racemic tramadol free base;

b) adding L-(+)-tartaric acid to the solution from step a); selectively precipitating (−)-tramadol enantiomer as (−)-tramadol L-(+)-tartrate, and separating the precipitated (−)-tramadol L-(+)-tartrate from the remaining mother liquor containing (+)-tramadol enantiomer;

c) treating the separated precipitate from step b) with additional alkali hydroxide to release the (−)-tramadol enantiomer in free base form;

d) converting the released (−)-tramadol enantiomer from step c) into a non-tartrate salt;

e) treating the mother liquor from step b) with additional alkali hydroxide to convert tartrate salts of (+)-tramadol enantiomer into free base form, and extracting (+)-tramadol free base from the mother liquor; and f) converting the extracted (+)-tramadol enantiomer from step e) into a non-tartrate salt.

8. A method according to claim 7, wherein said non-tartrate salts are hydrochloride salts, and said converting steps d) and f) are effected by treating an organic solvent solution of the respective tramadol enantiomer with trimethylchlorosilane and water.

9. A method according to claim 1, further comprising recycling the mother liquor from which the (+)-tramadol enantiomer free-base has been released, to the racemate separation process.

* * * * *